(12) United States Patent
Capaccioli et al.

(10) Patent No.: US 8,598,883 B2
(45) Date of Patent: Dec. 3, 2013

(54) MEASURING DEVICE OF THE ELECTRIC PROPERTIES OF SOLID OR LIQUID GEOLOGICAL SAMPLES

(75) Inventors: Simone Capaccioli, Pisa (IT); Mauro Lucchesi, Lucca (IT); Nicola Giovanni Bona, Milan (IT)

(73) Assignee: Eni S.p.A., Rome (IT)

( * ) Notice: Subject to any disclaimer, the term of this patent is extended or adjusted under 35 U.S.C. 154(b) by 390 days.

(21) Appl. No.: 12/992,294

(22) PCT Filed: May 12, 2009

(86) PCT No.: PCT/EP2009/003461
§ 371 (c)(1),
(2), (4) Date: Feb. 4, 2011

(87) PCT Pub. No.: WO2009/138240
PCT Pub. Date: Nov. 19, 2009

(65) Prior Publication Data
US 2011/0187375 A1  Aug. 4, 2011

(30) Foreign Application Priority Data

May 14, 2008  (IT) .............................. MI2008A0873

(51) Int. Cl.
*G01V 3/00*  (2006.01)
(52) U.S. Cl.
USPC ....................................................... 324/376
(58) Field of Classification Search
USPC ....................................................... 324/376
See application file for complete search history.

(56) References Cited

U.S. PATENT DOCUMENTS

| 4,734,649 A | 3/1988 | Barnaby |
| 5,095,273 A | 3/1992 | Kennedy et al. |

FOREIGN PATENT DOCUMENTS

| DE | 44 14 619 | 10/1995 |
| GB | 2 322 942 | 9/1998 |

OTHER PUBLICATIONS

International Search Report issued Aug. 21, 2009 in PCT/EP09/003461 filed May 12, 2009.

*Primary Examiner* — Bot Ledynh
(74) *Attorney, Agent, or Firm* — Oblon, Spivak, McClelland, Maier & Neustadt, L.L.P.

(57) ABSTRACT

The present invention relates to a measuring device (10) of the electric properties of solid or liquid geological samples, such as, for example, rocks, preferably from oil or gas reservoirs, and saturation fluids of the same, comprising a hollow body (11, 12) consisting of a first upper half-shell (11) and a second lower half-shell (12), the upper and lower half-shells (11, 12) coaxially sliding one inside the other, inside the body (11, 12) there being a housing seat (23) for a substantially cylindrical sample, two pairs of electrodes (13, 14) being envisaged facing the housing seat (23) for the injection of current into a sample and for the measurement of the voltage at the ends of the sample, characterized in that the pairs of electrodes (13, 14) are pairs of coplanar electrodes, each situated at one end of the housing seat (23).

15 Claims, 5 Drawing Sheets

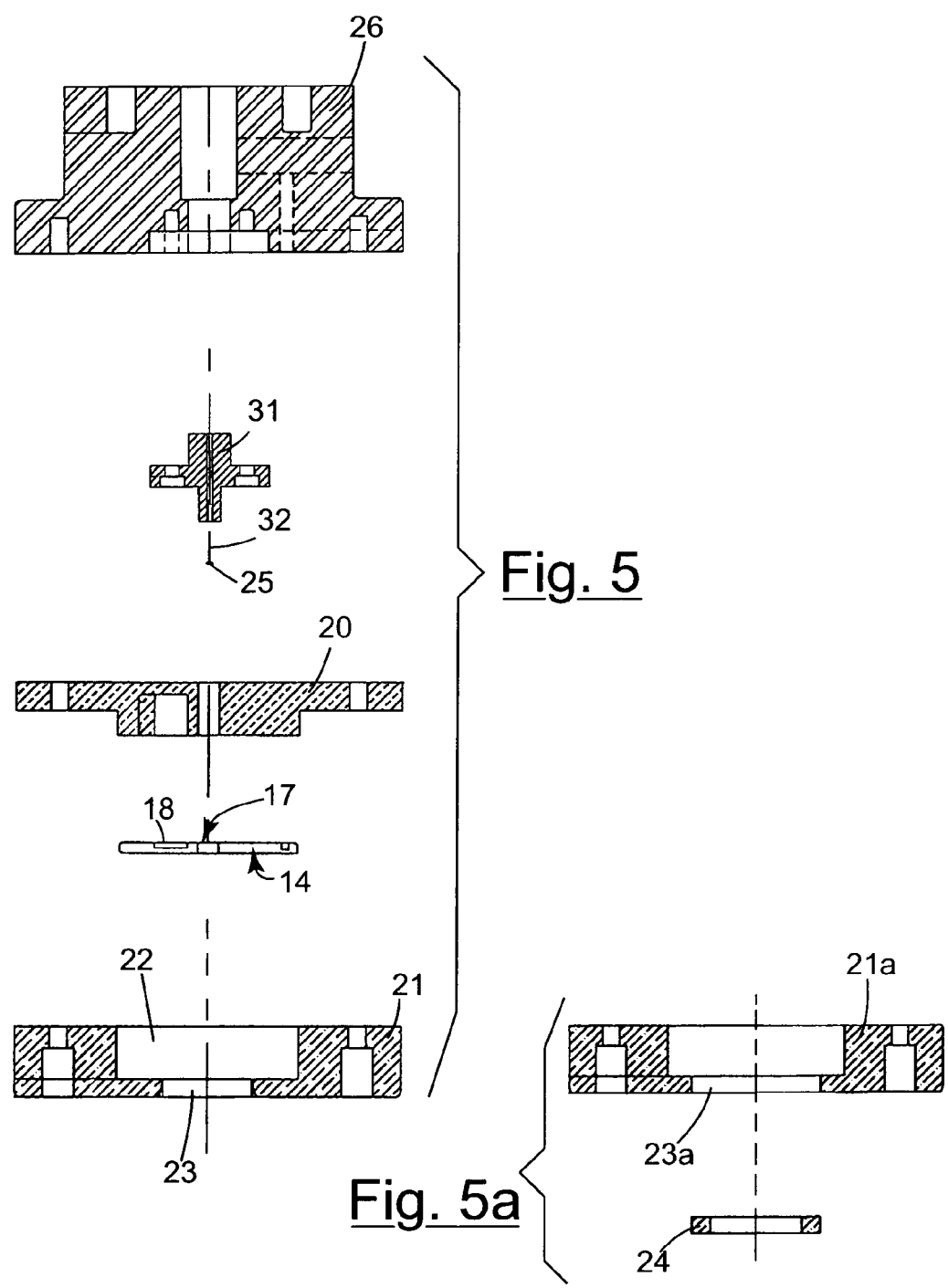

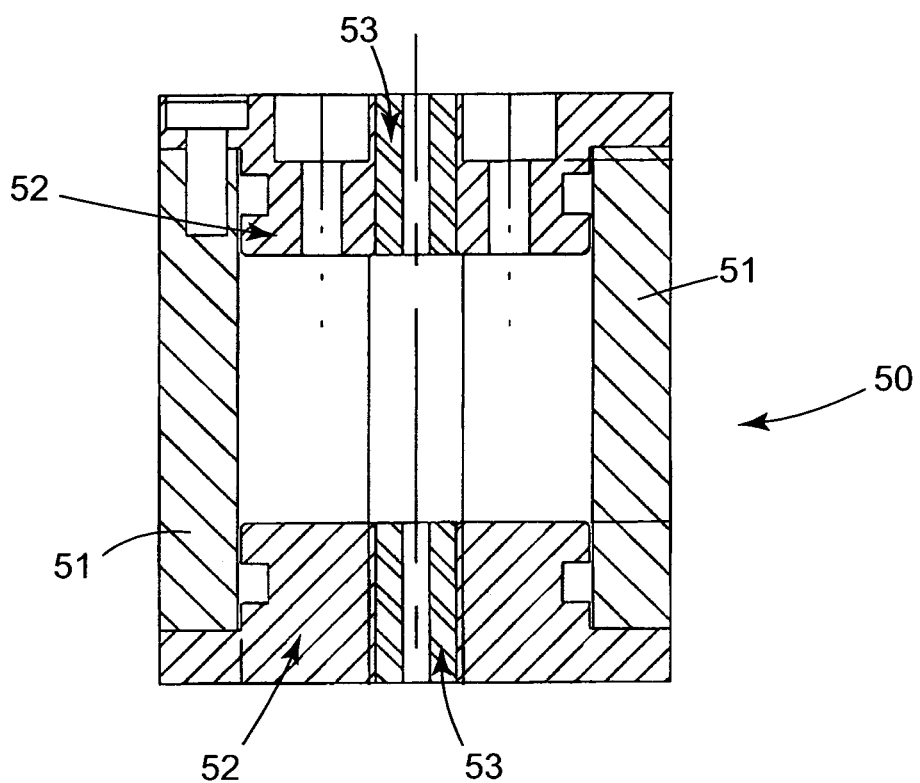

MEASURING DEVICE OF THE ELECTRIC PROPERTIES OF SOLID OR LIQUID GEOLOGICAL SAMPLES

The present invention relates to a measuring device of the electric properties of liquid or solid geological samples, such as rocks, preferably from gas or oil reservoirs and saturation fluids of the same.

The measurement of the low-frequency complex impedance, i.e. lower than 100 kHz, of rock samples from gas or oil reservoirs is normally effected through two complementary measurement techniques, with two or four electrode, respectively.

Single techniques are currently implemented by relative measuring devices comprising two or four electrodes, respectively. This implies the necessity of changing configuration according to the technique to be used and therefore the impossibility of applying these techniques in rapid succession.

In measuring devices with two electrodes, an electric contact is established between each electrode and a surface portion of the sample, an alternating electric current is injected and the potential difference which is established between the same electrodes, is measured.

The most common configuration used for cylindrical samples is that of a capacitor whose parallel and flat plates are in contact with the faces of said sample.

The complex impedance of the capacitor thus filled, or its admittance is measured when the frequency varies, through an impedance analyzer, which calculates the ratio between the potential difference at the electrodes and the current injected.

The complex impedance and admittance are defined by the following equations, respectively:

$$Z(\omega) = 1/(j\omega C_0 \in)$$

$$Y(\omega) = j\omega C_0 \in$$

wherein
$\omega$ is the frequency
$C_0$ is the capacity of the empty capacitor
$\in$ is the dielectric permittivity of the sample placed in the capacitor.

The dielectric spectrum $\in(\omega)$ of the sample is obtained from the complex impedance $Z(\omega)$ measured.

Although easy to produce, this known measuring device has various drawbacks.

In the case of measurements on rocks saturated with brine, systematic errors occur when the interface or contact resistances are not negligible with respect to that inside the sample, or when the electric contact between the sample and the electrodes is not satisfactory.

These problems can be reduced through treatment which is not easy to apply, such as, for example, by evaporating metallic layers on the faces of the rock sample. Notwithstanding this treatment, however, the above problems are generally not totally eliminated due to the roughness and incoherence of the rock surface.

Furthermore, a thin layer of mineral oil with insulating or slightly conductive characteristics may be present on the rock surface or a part of the water may evaporate, totally or partially drying the surface of the sample. This creates a contact impedance and a potential drop through the layer, with a consequent over-estimation of the resistance of the substrate of the sample, also called bulk resistance.

In order to avoid these inconveniences, the following solutions are known, which however can only be applied in particular cases:

(i) applying thin metal layers to the electrodes, which are sufficiently plastic and malleable to adapt to the rock surface, (ii) electrochemically depositing porous layers of platinum or silver chloride on the electrodes, (iii) using paper filters or porous silver filters soaked in the saturation brine to be inserted between sample and electrodes.

This latter expedient can make the contact resistance and that of the paper filter negligible, but only until the inner saturation level of brine is high. The evaporation of the liquid from the porous filter must therefore be avoided.

A reduction in the contact impedance, however, does not solve all the problems linked with the two-electrode measurement devices. For example, electrode polarization effects, in particular in low-frequency dielectric measurements on rocks with a high saturation and/or saturated by brine containing high concentrations of ionic carriers, can be particularly significant.

With respect to four-electrode measurement devices, only particular embodiments are known, which can be used for measuring the electric properties of the rocks. These embodiments have the specific characteristic that the impedance is measured using current injection electrodes and measurement electrodes of the potential, all situated on the lateral surface of the sample.

Finally, a measurement device is known, which is capable of using both the two-electrode and four-electrode techniques, with the same cell and at frequencies ranging from 10 Hz to 10 MHz.

This device includes two flat electrodes in contact with the sample faces to inject current and two rings as measurement electrodes of the voltage positioned on the lateral surface of the sample and suitably spaced from each other along the cylinder axis and in a symmetrical position with respect to the centre of the cylinder.

These devices therefore have the drawbacks indicated above, relating to the known devices with two electrodes, and also the drawback of inaccurate measurements when effected at high frequency through the four-electrode technique, due to the restricted contact surface of the rings, which makes the capacity of the same very small.

An objective of the present invention is to overcome the above drawbacks and, in particular, to provide a measuring device of the electric properties of geological samples which offers the possibility of applying two- and four-electrode techniques in a rapid sequence and with sufficient accuracy.

Another objective of the present invention is to provide a measuring device of the electric properties of geological samples which, when used for effecting two-electrode measurements, is not subjected to systemic errors or to over-estimation of the substrate resistance.

A further objective of the present invention is to provide a measuring device of the electric properties of geological samples which, when used to effect four-electrode measurements, offers accurate measurements even when effected at high frequency.

These and other objectives according to the present invention are achieved by providing a measuring device of the electric properties of geological samples as specified in claim 1.

Further characteristics of the device are object of the dependent claims.

The characteristics and advantages of a measuring device of the electric properties of geological samples according to the present invention will appear more evident from the following illustrative and non-limiting description referring to the enclosed schematic drawings, in which:

FIG. 5 is an exploded sectional view of a set of elements of the measuring device of FIG. 4;

FIG. 5a is a sectional view of an alternative embodiment of the annular element of the measuring device according to the present invention;

FIG. 7 is a sectional view of the liquid sample-holder device in the assembled configuration of FIG. 6a.

Figure 1:
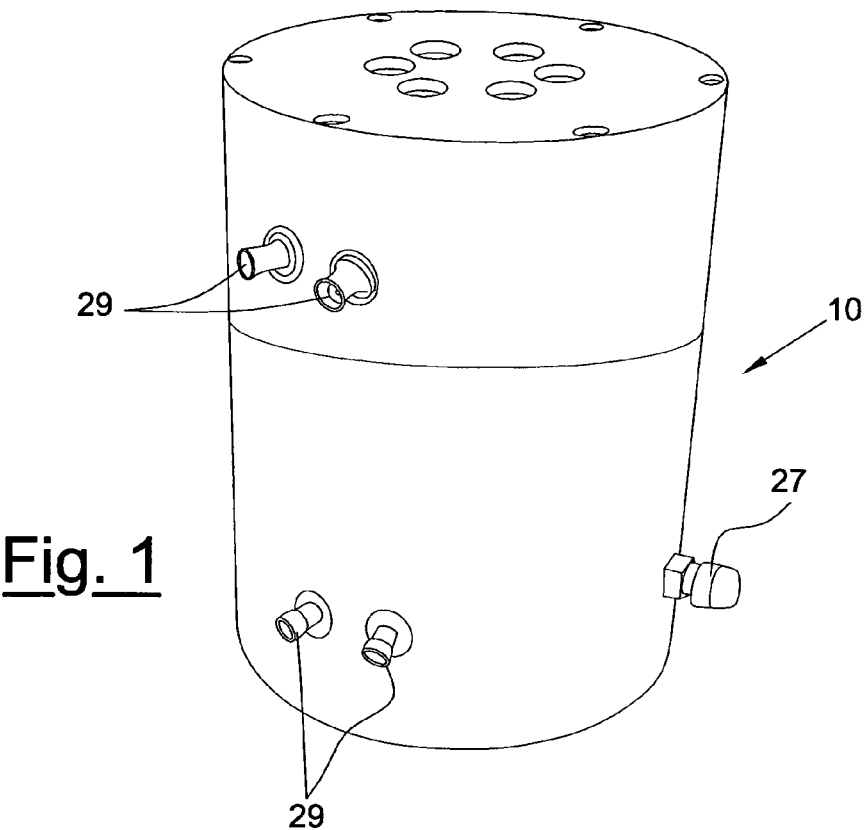
FIG. 1 is a perspective view of a measuring device of the electric properties of geological samples according to the present invention.
Figure 2:
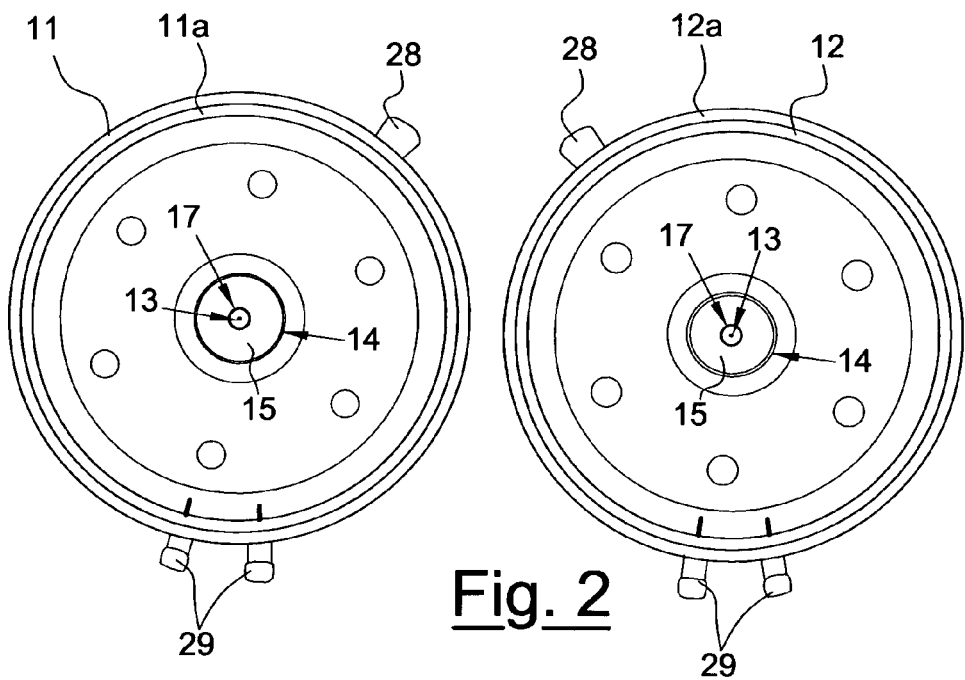
FIG. 2 is a view from above of the upper and lower half-shells of the measuring device of FIG. 1 in an open configuration.
Figure 3:
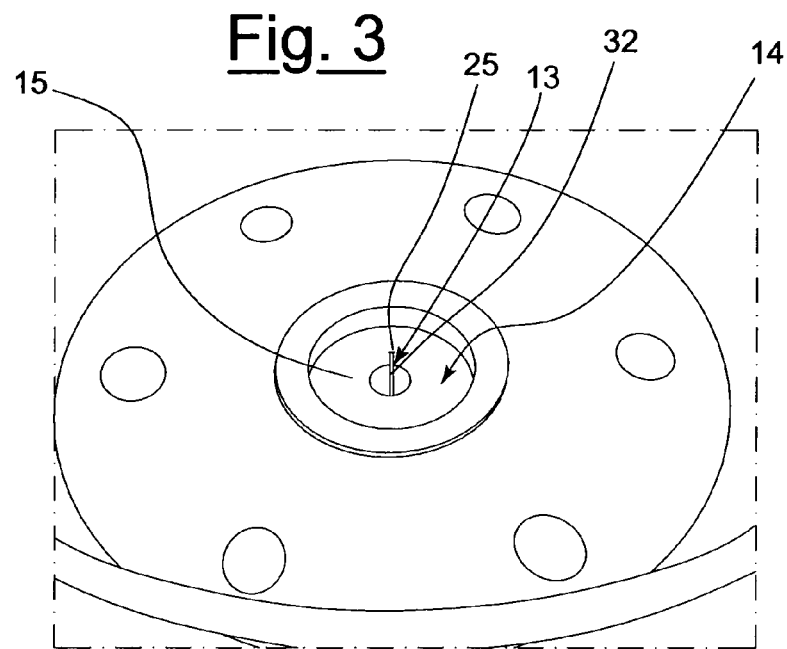
FIG. 3 is an enlarged view of the electrodes used in the measuring device according to the present invention.
Figure 4:
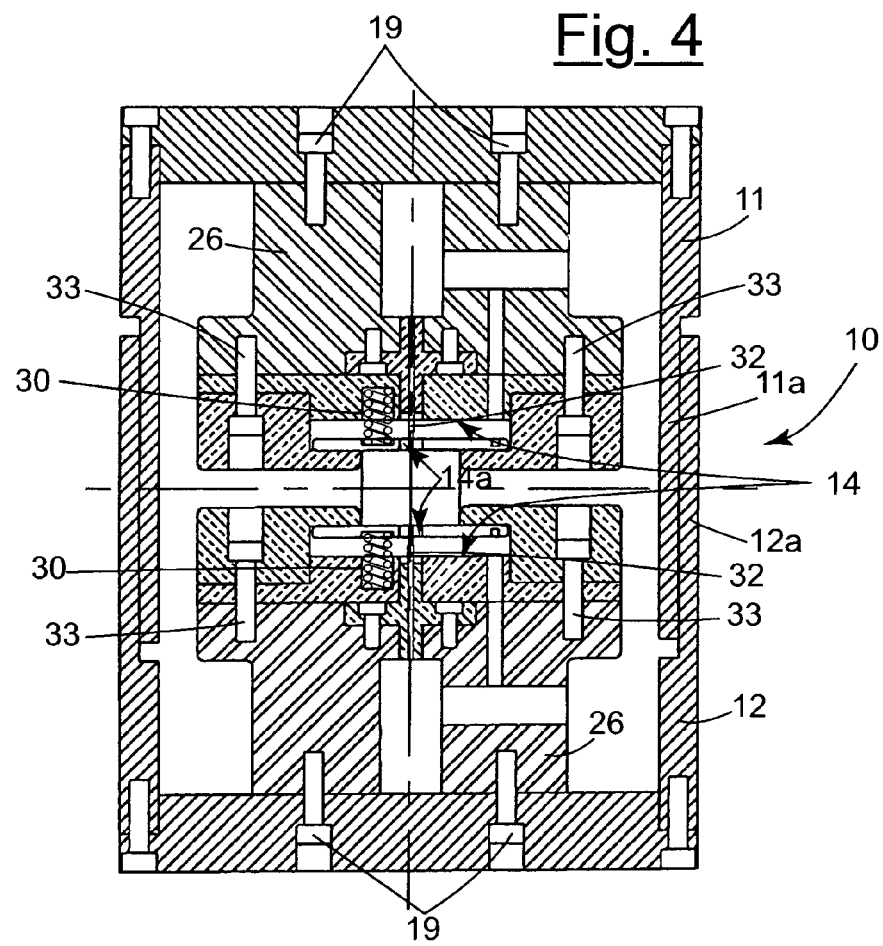
FIG. 4 is a sectional view of the measuring device of FIG. 1.

With reference to the figures, a preferred and non-limiting embodiment is shown of a device for the measurement of the electric properties of geological samples, indicated as a whole with 10.

The measuring device 10 comprises a hollow body, preferably cylindrical, consisting of two half-shells 11,12 one coaxially sliding over the other, partially overlapping in correspondence with a portion 11a,12a having a reduced thickness.

A pair of coplanar contacts 13,14 is advantageously situated on each base of the half-shells 11,12.

Each pair of coplanar contacts comprises a first electrode for the injection of the current 14, having a substantially flat shape and provided with a pass-through hole 17, in correspondence with which a second electrode is arranged for measuring the voltage (13).

The first injection electrodes of the current 14 are preferably circular in shape and the pass-through hole 17 is positioned in the centre of the same. Furthermore, in a preferred embodiment, the first electrodes 14 are made of gold-plated brass.

On the surface 14a of the first current injection electrode 14 which faces the inside of the measuring device, a sheet 15 made of noble metal, preferably pure gold, not work-hardened by cold processing, is welded.

The sheet 15 is advantageously extremely plastic and deforms by adhering to the surface of the geological sample subjected to measurement, when a sufficiently high pressure is exerted on the electrode 14. This sheet 15 also protects the first electrode 14 from corrosion due to the brine.

On the other side of the first current injection electrode 14, there is a plurality of circular housings 18 for first elastic means 30, such as, for example, compression springs, preferably uniformly distributed.

In the embodiment shown, there are three housings arranged at 120° from each other.

In this preferred embodiment, the springs 30 are made of harmonic steel wire with a diameter of 1.25 mm and have a diameter of 9.25 mm, a free length of 22.0 mm and a minimum operative length of 10.5 mm (useful coils 5.5). The constant of these springs 30 is preferably 8.92 N/mm.

In this preferred and non-limiting embodiment, for a compression of 4 mm, generally equal to a half of the maximum compression admitted by the geometry of the measuring devices 10, it is necessary to exert a force of 35.68 N on each spring 30, i.e. an overall force of 107 N corresponding to a total weight force of 10.9 kg.

Assuming a sample surface of about 5 cm$^2$, in order to exert the above compression, it is necessary to apply a pressure of 2 atm.

The springs 30 which support the first circular current injection electrode 14 are housed inside a supporting element 20 made of insulating material, preferably Teflon®.

An annular element 21—also made of insulating material, preferably Teflon®, whose function is to maintain the first current injection electrode 14 in position and drive it during the phase in which the contact is established, by compression, between said electrode 14 and the sample—is tightened onto the supporting element 20.

The annular element 21 has, in its lower part, a first housing 22 for the first current injection electrode 14, and in the upper part, a second housing 23 for receiving the cylindrical rock samples subjected to measurement.

The two opposite second housings 23, each corresponding to one of the two pairs of electrodes 13,14, form, inside the measuring device 10, a housing seat for the samples undergoing measurement.

In the alternative embodiment illustrated in FIG. 5a, the annular element 21a has a second housing 23a with such dimensions as to house cylindrical samples having a large diameter, and a reducing ring 24 suitable for making the second housing 23a appropriate for also housing samples having a smaller diameter.

This device makes it possible to pass, in a simple way, from the measurement of samples with a smaller diameter, to that of samples with a larger diameters, by simply inserting or removing the reducer ring 24.

Thanks to the plurality of springs 30, the current injection electrodes 14 are sufficiently free to bend to adapt themselves to the faces of the cylindrical sample, should these not be perfectly parallel.

The second electrode for the measurement of the voltage 13, concentric to the first current injection electrode 14, consists of a spring contact or probe, preferably gold-plated.

Said probe 13 includes in its interior second elastic means which assure contact with the sample. These second elastic means preferably have an elastic constant of 1.2 N/mm.

The probe 13 consists of a jack 32, preferably made of copper-beryllium, gold-plated on nickel, and a housing tube 31 or plug, preferably made of metallic gold-plated alloy. The overall resistance of the probe 13 is preferably lower than 15 mOhm.

The free terminal part 25 of the jack 32 which, in stand-by position, exceeds the plane of the first electrode 14, is brought to the level of the plane of said first electrode 14 by charging the sample. The consequent compression of the jack 32 assures a good contact between the probe 13 and the sample.

In the case of second elastic means dimensioned as described above, in fact, the force exerted on the end portion 25 of the jack 32 is equal to 6 N and the pressure exerted on the sample by the free end portion 25 of the jack 32 is in the order of about ten atmospheres.

In order to guarantee a good contact with the surface of the sample, the free end portion 25 of the jack is enlarged and preferably in the form of a spherical drop, or alternatively, a spherical drop in a malleable conductive material, and preferably tin or indium, it is welded in correspondence with said end part 25.

Every time the second electrode 13 is compressed against the surface of the sample, the enlargement 25 is deformed and adheres to the surface of the sample, with the result of reducing the contact resistance.

The diameter of the free end part 25 of the jack 32 in the form of a spherical drop is preferably 2.54 mm.

The second electrode 13 is arranged concentrically in the hole 17 of the first current injection electrode 14 and is separated from this by a circular space much larger in extension, in the material, of the double layer of charges produced by the polarization of the electrodes which is in an order of magnitude of nanometres.

In a preferred embodiment, the probes 13 have a milled surface which favours a better contact in the case of rugged or incoherent samples.

This configuration with a milled surface also proves to be particularly suitable in the presence of layers of mineral oil accumulated on the face of the sample, as the teeth of the milling can penetrate the first layers of the sample coming into contact with the more homogeneous portions of the sample and measure more accurate potential differences.

The probe 13 is assembled on the supporting body 26 made of insulating material, preferably Teflon®, and is rigidly blocked, preferably by means of screws 33 also made of insulating material such as nylon for example, to the supporting element 20 which contains the springs 30 and the first current injection electrode 14.

The unit consisting of the supporting elements 20 and annular elements 21, the supporting body 26 and also the first and second electrode 13, 14 is, in turn, rigidly anchored to the relative half-shell 11, 12 which is preferably made of steel, through suitable fixing means 19 made of insulating material.

In this way, the cylindrical body consisting of the two half-shells 11, 12 acts as a metallic shield and, according to requirements, can be connected to the mass or left floating.

Said cylindrical body 11, 12 exerts different functions among which the main ones are:

maintaining the electrodes 13, 14 and the sample constantly aligned;

allowing the electrodes 13, 14 to approach each other to ensure and maintain the electric contact with the sample;

insulating the sample and electrodes 13, 14 from external electromagnetic noise; and keeping the sample in an environment with a controlled humidity.

In order to monitor the conditions of the environment inside the cylindrical body 11, 12, there is a temperature sensor and a relative humidity sensor accessible from the outside through a connector 27 present in the lower part of the cylindrical body 11, 12.

The relative humidity of the measurement environment is controlled, by putting the interior of the cylindrical body 11, 12 in contact with an environment having a defined humidity, through a gas connection 28 applied to the upper part 11 of the cylindrical body.

The Applicant observed, during some tests, that the level of relative humidity measured by the sensor, once the sample had been inserted and the measuring device 10 closed, increases until it reaches a stable value.

Figure 6A:
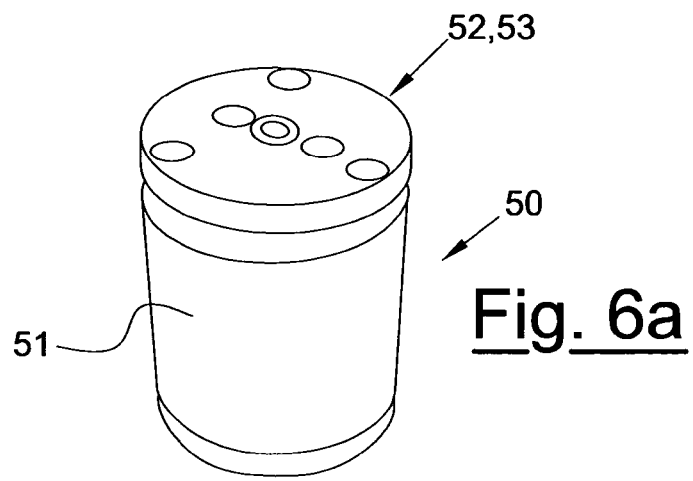
FIG. 6a is a perspective representation in an assembled configuration of a liquid sample-holder device, used when the measuring device according to the present invention is adopted for measuring the electric properties of liquid geological samples.
Figure 6B:
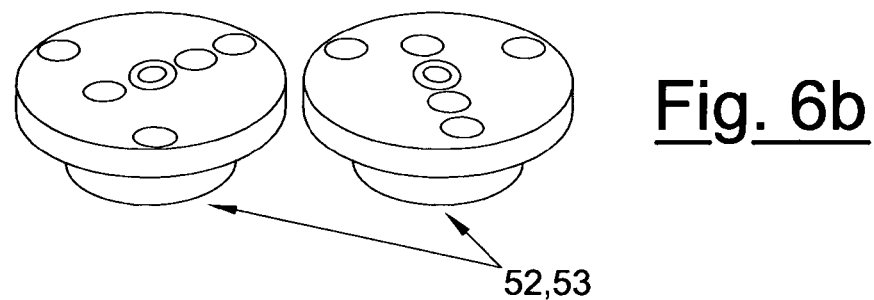
FIG. 6b is a perspective view of the bases of the liquid sample-holder device of FIG. 6a in which the outer sides are facing upwards.
Figure 6C:
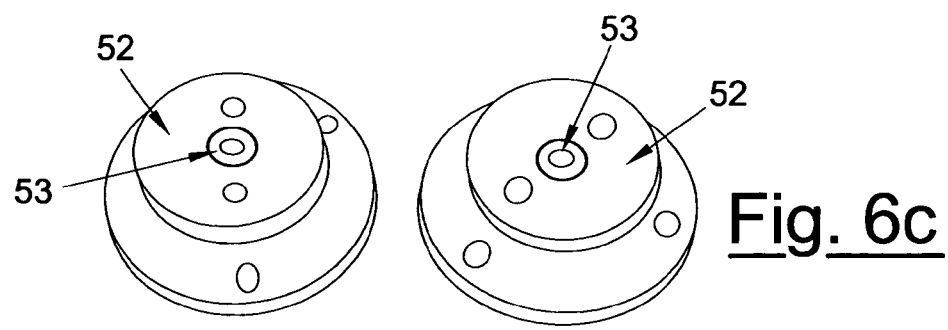
FIG. 6c is a perspective view of the bases of the liquid sample-holder device of FIG. 6a in which the inner sides are facing upwards.

With reference to FIGS. 6a-6c and 7, these show a liquid sample-holder device 50 which can be inserted in the measuring device 10 according to the present invention when the electric properties of a liquid sample are to be determined.

Said liquid sample-holder device 50 preferably has outer dimensions typical of a rock core sample, i.e. 38 mm in diameter and 44 mm in height.

Said device 50 is then inserted in the measuring prototype 10 in the place of a solid geological sample and allows various tests to be effected in addition to calibrations with reference liquids in the same configuration in which the measurements are subsequently effected.

The lateral surface consists of a cylindrical hollow body 51 made of plastic material, such as nylon.

A pair of contacts 52, 53 is arranged at each of the two ends of the hollow cylindrical body 51. Said pair of contacts 52, 53 is produced with a first outer perforated electrode 52 for the injection of the current and with a second concentric electrode 53, insulated by a ring made of an insulating material, preferably Teflon®.

The first and second electrode 52, 53 preferably have dimensions of 38 mm and 2 mm respectively.

Inside the hollow body 51, the diameter of the first metallic electrode 52 is preferably 25.4 mm. The distance between the two pairs of electrodes 52, 53 is preferably 20.3 mm.

A series of screws allows access to the interior of the hollow body 51 thus making it possible to fill and empty the liquid sample-holder device 50 of the relative samples.

The two pairs of contacts 52, 53 are screwed onto the hollow cylindrical body 51 and the sealed closure is ensured by the rubber O-ring and/or Teflon® tape (not illustrated).

The functioning of the measuring device 10 of the electric properties of geological samples according to the present invention is the following.

In the case of a solid sample, a cylindrical core of this sample is inserted in one of the two second housings 23 inside the metallic body 11, 12.

Otherwise, in the case of a liquid sample, the sample is introduced into the liquid sample-holder device 50 which is then inserted in the second housings 23 in the place of the core of solid sample.

The measuring device 10 is then closed and an increasing pressure is exerted, for example between 2 and 4 atmospheres, on the two bases of the half-shells 11, 12 by a hydraulic press until a good electric contact is established between the electrodes 13, 14 and the sample or liquid sample-holder device 50.

The signals are made accessible to an external impedance analyzer by means of four connectors 29, preferably of the BNC type, electrically insulated by the cylindrical body 10.

The connectors 29 are preferably connected to the respective electrodes 13, 14 with protected coaxial wires.

In this way, the external conductor of each wire, connected with each external BNC conductor 29, can float freely regardless of the potential of the cylindrical body 11, 12 which can be freely earthed.

The electric insulation between the electrodes 13, 14 and towards the mass is ensured by the use of insulating material, such as for example Teflon®, for the annular elements 21 which support the sample and are in contact with the electrodes 13, 14 and other insulating material such as nylon for example, with respect to the fixing means 19 which ensure the unification of supports 20, 21, 26 and electrodes 13, 14 with the metallic cylindrical body 11, 12.

A further centering ring made of insulating material (not illustrated) which slides inside the cylindrical body 11, 12 can be used for guiding the bases of the longer samples towards the housings 23 on the measuring electrodes 13, 14.

The characteristics of the device, object of the present invention, are evident from the above description, as also the relative advantages.

The measuring device of the electric properties of geological samples according to the present invention makes it possible to effect measurements with both two and four electrodes on the same sample, without the necessity of having to change configuration. The two measuring techniques can therefore be applied in rapid succession.

Furthermore, the particular form of the electrodes makes systematic errors and the over-estimation of the resistance of the substrate negligible, when the device is commanded to effect measurements with two electrodes, and also offers accurate measurements when effected at high frequency, when the device is commanded to effect measurements with four electrodes.

Finally, the device thus conceived can obviously undergo numerous modifications and variants, all included in the invention, furthermore all the details can be substituted by technically equivalent elements. In practice, the materials used, as also the dimensions, can vary according to technical requirements.

The invention claimed is:

1. A measuring device of the electric properties of geological samples comprising:
    a hollow body consisting of a first upper half-shell and a second lower half-shell, the upper and lower half-shells coaxially sliding one inside the other, inside said body, there being a housing seat for a substantially cylindrical sample, two pairs of electrodes being envisaged facing said housing seat for the injection of current into a sample and for measuring the voltage at the ends of said sample, wherein
    said pairs of electrodes are pairs of coplanar electrodes, each situated at one end of said housing seat.

2. The measuring device of the electric properties of geological samples according to claim 1, wherein each of said pairs of coplanar electrodes comprises a first current injection electrode having a substantially flat form and equipped with a pass-through hole and a second electrode for measuring the voltage situated in correspondence with said hole.

3. The measuring device of the electric properties of geological samples according to claim 2, wherein a sheet made of a noble metal is welded on a surface of said first current injection electrode which internally faces the measuring device.

4. The measuring device of the electric properties of geological samples according to claim 2, wherein said first current injection electrode is supported by a plurality of first elastic members housed inside a supporting element made of insulating material.

5. The measuring device of the electric properties of geological samples according to claim 4, wherein an annular element is tightened onto said supporting element, made of an insulating material comprising, on a first side, a first housing suitable for receiving said first current injection electrode and, on a second side, a second housing suitable for receiving said sample, said housing seat consisting of two second opposite housings each corresponding to one of said two pairs of coplanar electrodes.

6. The measuring device of the electric properties of geological samples according to claim 5, wherein said annular element comprises a reducer ring suitable for reducing the dimensions of said second housing.

7. The measuring device of the electric properties of geological samples according to any one of claims 4 to 6, wherein said second electrode for measuring the voltage consists of a spring contact provided with second elastic member which act on the basis of a jack housed in a housing tube.

8. The measuring device of the electric properties of geological samples according to claim 7, wherein a free end part of said jack comprises an enlargement made of a malleable conductive material.

9. The measuring device of the electric properties of geological samples according to claim 7, wherein said spring contact has a milled surface.

10. The measuring device of the electric properties of geological samples according to claim 7, wherein said spring contact is assembled on a supporting body made of insulating material tightened onto said supporting element of said first electrode.

11. The measuring device of the electric properties of geological samples according to claim 10, wherein a set consisting of said supporting element, said annular element, said supporting body and said first and second electrode is rigidly anchored to the relative lower or upper half-shell.

12. The measuring device of the electric properties of geological samples according to claim 1, wherein in said housing seat a liquid sample-holder device is housed, consisting of a hollow cylindrical body, there being a pair of contacts at each of the ends of said hollow cylindrical body.

13. The measuring device of the electric properties of geological samples according to claim 12, wherein said pair of contacts comprises a first outer perforated electrode for the injection of current and with a second electrode concentric to said first electrode and insulated from the same by a ring made of an insulating material.

14. The measuring device of the electric properties of geological samples according to claim 1, wherein said hollow body comprises a connector for the external connection of a sensor.

15. The measuring device of the electric properties of geological samples according to claim 1, further comprising:
    a gas connection suitable for putting the interior of said hollow body in contact with a pre-established humidity environment and/or with a device which measures the humidity inside said hollow body.

* * * * *